(12) United States Patent
Oh et al.

(10) Patent No.: US 8,927,755 B2
(45) Date of Patent: Jan. 6, 2015

(54) I- AND II-TYPE CRYSTALS OF L-ALPHA-GLYCERYL PHOSPHORYL CHOLINE, AND METHOD FOR PREPARING SAME

(75) Inventors: Min-Keun Oh, Bucheon-si (KR); Ki-Nam Kim, Suwon-si (KR); Ki-Hyeong Seo, Pyeongtaek-si (KR); Dae-Gil Kwon, Gwangmyeong-si (KR)

(73) Assignee: Hanseochem Co., Ltd., Pyeongtaek-Si (KR)

( * ) Notice: Subject to any disclaimer, the term of this patent is extended or adjusted under 35 U.S.C. 154(b) by 0 days.

(21) Appl. No.: 14/003,276

(22) PCT Filed: Feb. 22, 2012

(86) PCT No.: PCT/KR2012/001331
§ 371 (c)(1),
(2), (4) Date: Sep. 5, 2013

(87) PCT Pub. No.: WO2012/124907
PCT Pub. Date: Sep. 20, 2012

(65) Prior Publication Data
US 2013/0345464 A1 Dec. 26, 2013

(30) Foreign Application Priority Data
Mar. 14, 2011 (KR) .......................... 10-2011-0022392
Mar. 14, 2011 (KR) .......................... 10-2011-0022393

(51) Int. Cl.
*C07F 9/09* (2006.01)

(52) U.S. Cl.
CPC .................................... *C07F 9/091* (2013.01)
USPC .......................................... 558/146; 558/169

(58) Field of Classification Search
None
See application file for complete search history.

(56) References Cited

U.S. PATENT DOCUMENTS 5,523,450 A   6/1996   Evans

FOREIGN PATENT DOCUMENTS

| EP | 0486100 | 5/1992 |
|---|---|---|
| JP | 05-092982 | 4/1993 |
| JP | 2007-269657 | 10/2007 |
| KR | 10-2007-0119176 | 12/2007 |
| KR | 10-2009-0084194 | 8/2009 |

*Primary Examiner* — Sun Jae Yoo
(74) *Attorney, Agent, or Firm* — Lexyoume IP Meister, PLLC (57) ABSTRACT

The present invention relates to I- and II-type crystals of L-α-glyceryl phosphoryl choline, and to a method for preparing same. More particularly, the present invention relates to noble I- and II-type anhydride crystals of L-α-glyceryl phosphoryl choline, which have a higher purity than conventional liquid L-α-glyceryl phosphoryl choline, and one advantage of which is that formulations and dosages of pharmaceuticals are easily modified, and another advantage of which is that the hygroscopicity of the crystals are much lower than that of conventional polymorphic crystals, providing excellent stability during storage. The present invention also relates to a method for preparing the I- and II-type crystals of L-α-glyceryl phosphoryl choline.

4 Claims, 8 Drawing Sheets

I- AND II-TYPE CRYSTALS OF L-ALPHA-GLYCERYL PHOSPHORYL CHOLINE, AND METHOD FOR PREPARING SAME

TECHNICAL FIELD

The present invention relates to type I and type II crystals of L-alpha-glyceryl phosphoryl choline and to a method for preparing same. More specifically, the present invention relates to preparation of new type I and type II crystals of L-alpha-glyceryl phosphoryl choline which have more advantages than the conventional liquid L-alpha-glyceryl phosphoryl choline: The purity is higher, the formulations and dosages are more easily modified in the sense of manufacturing pharmacy, and the storage stability is better due to a much lower hygroscopic property than conventional polymorphic crystals.

BACKGROUND TECHNOLOGY

L-alpha-glyceryl phosphoryl choline (GPC hereunder) expressed by the following chemical formula I is a substance known to be used to improve brain function and treat dementia.

Chemical Formula 1

The conventional method of preparing L-alpha-glyceryl phosphoryl choline is largely divided into the pure synthetic method and the extraction method in which the choline is extracted from recithin, a by-product of bean. For example, the methods introduced in such patents as European patent No. 486.100, Italian Patent No. 1,243,724, and Italian Patent No. 1,247,496 are the pure synthetic method, and the methods introduced in such patents as U.S. Pat. No. 5,250,719, British Patent No. 2,058,792, and European Patent No. 217,765 are the recithin extraction method. The conventional GPC prepared with these methods is obtained at the liquid state containing a considerable amount of water.

Meanwhile, the method for crystallization of the above-mentioned liquid L-alpha-glyceryl phosphoryl choline is also known. First of all, in J. Am. Chem. Soc. 70, 1394-1399 (1948), it was reported that the water-containing GPC prepared with the pure synthetic method could be solidified from the alcohol solution, but the detailed crystallization method and the crystalline structure were not mentioned.

In Korean Patent No. 262281 (registration date: Apr. 29, 2000), a new method of preparing GPC was introduced: First, GPC was synthesized by the alcoholysis deacylation reaction in a reactor containing a basic ion exchange resin and the lipophilic impurities are removed by using a non-polar adsorption resin. Then, the above-mentioned GPC was dissolved in methanol and n-butanol whose amount was 20 times the methanol solution was added to the methanol solution. Finally, the total solution was concentrated in vacuum, cooled, and filtered to recover an anhydrous form of crystal. In this method, however, though only the formation of very hygroscopic fine crystals was reported, details on the crystalline structure were not mentioned.

And, in Korean Patent No. 966,627 (registration date: Jun. 20, 2010), a method of preparing GPC hydrochloride, as expressed by chemical formula 2, by using a crystallization solvent composed of C1-C6 alcohols, C1-C6 ketones and their mixtures, was introduced but again the crystalline structure was not mentioned.

Chemical Formula 2

Like this, though efforts have been made to crystallize GPC and the possibility of crystallization has been proposed, details on the crystallization conditions or the crystalline structure has not been mentioned. And the raw material of crystalline GPC available for industrial applications has not produced yet.

DETAILED DESCRIPTION OF INVENTION

Technical Problem

As observed above, all the raw materials of GPC which have been produced industrially so far are at the liquid state and the GPC medicines under current sale are limited to soft capsules made by using the above-mentioned liquid raw material. In such soft capsules, however, the active component is likely to dissolve the gelatin capsule as the time passes, complex manufacturing facilities are required, and not only a preserving agent should be used to prevent microbial degeneration but also they are inconvenient for patients to take.

Thus, while conducting research on powder-type GPC in order to manufacture GPC tablets which may replace GPC soft capsules, the present inventors confirmed that all the GPC crystals obtained with the crystallization method known so far are polymorphic ones and that there exist new Type I and Type II crystals which have totally different crystalline properties from the above-mentioned polymorphic crystal. And the present invention was completed by developing an effective method of producing industrially each of the above-mentioned Type I and Type II crystals on the basis of the use of seed crystal and the optimized crystallization conditions.

The objective of the present invention is to provide the Type I and Type II crystals of L-alpha-glyceryl phosphoryl choline and the method of preparing same.

Technical Solution

According to the present invention, Type I crystal of L-alpha-glyceryl phosphoryl choline is characteristic in that it has an onset temperature of 147° C. and an absorption peak of 150° C. on the basis of the differential scanning calorimetry (DSC) analysis and it also has diffraction patterns where 2Θ-diffraction angles are 9/8±0.2°, 12.0±0.2°, 14.3±0.2°, 15.8±0.2°, and 19.6±0.2° on the basis of the powder X-ray diffraction (XRD) analysis.

In addition, the manufacturing method of the above-mentioned Type I crystal is characterized by; A) a step of decreasing the water content to 6-12% by concentrating ordinary liquid L-alpha-glyceryl phosphoryl choline at 45-65° C.; B) a step of dissolving the concentrated L-alpha-glyceryl phosphoryl choline obtained from the step A) into alcohol solution whose amount is 1 to 5 times that of the above-mentioned concentrated choline and then cooling the entire solution to 5-20° C.; and C) a step of feeding, as the seed crystal, 0.1-0.5 mole % of L-alpha-glyceryl phosphoryl choline Type I crystal into the alcohol solution of L-alpha-glyceryl phosphoryl choline obtained from the step B) process, aging the mixed solution while it is stirred at 30-60 rpm for 2 to 5 hours, and then filtering the extracted crystal.

According to the present invention, Type II crystal of L-alpha-glyceryl phosphoryl choline is characteristic in that it has an onset temperature of 62° C./an absorption peak of 66° C. and an onset temperature of 141° C./an absorption peak of 145° C. on the basis of the differential scanning calorimetry (DSC) analysis and it also has diffraction patterns where $2\Theta$-diffraction angles are $10.3\pm0.2°$, $12.2\pm0.2°$, $13.4\pm0.2°$, $14.8\pm0.2°$, and $20.6\pm0.2°$ on the basis of the powder X-ray diffraction (XRD) analysis.

In addition, the manufacturing method of the above-mentioned Type II crystal is characterized by; A) a step of decreasing the water content to 6-12% by concentrating ordinary liquid L-alpha-glyceryl phosphoryl choline at 45-65° C.; B) a step of dissolving the concentrated L-alpha-glyceryl phosphoryl choline obtained from the step A) process into alcohol solution whose amount is 1 to 5 times that of the above-mentioned concentrated choline and then cooling the entire solution to 5-20° C.; and C) a step of feeding, as the seed crystal, 0.1-0.5 mole % of L-alpha-glyceryl phosphoryl choline Type II crystal into the alcohol solution of L-alpha-glyceryl phosphoryl choline obtained from the step B), aging the mixed solution without agitation for 2 to 5 hours and then filtering the extracted crystal.

Advantageous Effects

According to the present invention, Type I and Type II crystals of L-alpha-glyceryl phosphoryl choline are effective in producing a variety of medicines with high drug compliance to patients since the purity is higher and the formulations and dosages are easier in the sense of manufacturing pharmacy than those of the conventional liquid raw material of L-alpha-glyceryl phosphoryl choline.

In addition, the above-mentioned crystals have advantages that the storage stability is excellent and they are easy to handle during the medication process due to much lower hygroscopic property than the conventional polymorphic crystal.

BEST MODES FOR CARRYING OUT THE INVENTION

Type I crystal of L-alpha-glyceryl phosphoryl choline of the present invention is characteristic in that it has, as an anhydride, an onset temperature of 147° C. and an absorption peak of 150° C. in the differential scanning calorimetry (DSC) analysis and has diffraction patterns wherein $2\Theta$-diffraction angles are $9/8\pm0.2°$, $12.0\pm0.2°$, $14.3\pm0.2°$, $15.8\pm0.2°$, and $19.6\pm0.2°$ in the powder X-ray diffraction (XRD) analysis.

The above-mentioned Type I crystal of L-alpha-glyceryl phosphoryl choline has the tetrahedral structure of the tetragonal system in which the size of crystal grain is uniform at about 95-115 μm and the consolute temperature is about 150° C. (1 degree/minute). And since the hygroscopicity is low in comparison with the conventional polymorphic crystal, though the raw material with a water content of 0.1% is left under a humidity condition of 30% for about 10 hours the water content increases only slightly to 0.2%.

In addition, Type II crystal of L-alpha-glyceryl phosphoryl choline is, as a mono-hydrate, characteristic in that it has an onset temperature of 62° C./an absorption peak of 66° C. and an onset temperature of 141° C./an absorption peak of 145° C. on the basis of the differential scanning calorimetry (DSC) analysis and it also has diffraction patterns where $2\Theta$-diffraction angles are $10.3\pm0.2°$, $12.2\pm0.2°$, $13.4\pm0.2°$, $14.8\pm0.2°$, and $20.6\pm0.2°$ on the basis of the powder X-ray diffraction (XRD) analysis.

The above-mentioned Type II crystal of L-alpha-glyceryl phosphoryl choline has the polyhedral form of the hexagonal system in which the size of crystal grain is uniform at about 200-300 μm and the consolute temperature is about 66° C. (1 degree/minute). And since the hygroscopicity is low in comparison with the conventional polymorphic crystal, though the raw material with a water content of 6.5% is left under a humidity condition of 30% for about 10 hours, the water content remains almost unchanged at 6.5%.

For reference, the conventional polymorphic crystal is relatively very hygroscopic. In case the raw material with a water content of 2.9% is left under a humidity condition of 30%, as time passes, it absorbs moisture from air to reach a water content of 4.2% after 10 hours. If the hygroscopic property is large like this, special handling required since the weight and physical property are likely to change during the raw material storage or the medication process.

The preparation method of the above-mentioned Type I and Type II crystals of L-alpha-glyceryl phosphoryl choline consists of the following 3 steps:

A) Concentration Step of Liquid L-Alpha-Glyceryl Phosphoryl Choline

First of all, ordinary L-alpha-glyceryl phosphoryl choline is concentrated to decrease the water content to 6-12%. At this time, if the above-mentioned concentration temperature is below 45° C. or above 65° C., lamp black substances are created to cause difficulties during the purification process. And if the water content after concentration is below 6%, the undesirable polymorphic crystal may be generated. Conversely, if it is above 12%, the yield of crystallization falls a great deal, which is undesirable.

For reference, the moisture content for the raw material of ordinary liquid L-alpha-glyceryl phosphoryl choline is about 15-18%. Such liquid raw material may be used without concentration. In this case, however, since the yield of crystallization is low, it is desirable to concentrate it to a water content of 6-12%.

In case the liquid L-alpha-glyceryl phosphoryl choline with a water content of 15-18% is used as the starting material, the water content decreases to 6-12% if it is concentrated at 45-65° C. for 8-10 hours.

B) Dissolution Step of Concentrated L-Alpha-Glyceryl Phosphoryl Choline

Next, the L-alpha-glyceryl phosphoryl choline concentrated in the above-mentioned A) step is fed and dissolved into an alcohol solution, the foreign materials are removed by filtering the mixed solution with a membrane filter, and then it is cooled to 5-20° C.

At this time, ethanol and isopropyl alcohol may be used as the above-mentioned alcohol solution for crystallization and the alcohol amount used is 1 to 5 times the amount of the concentrated L-alpha-glyceryl phosphoryl choline, preferably 2 to 5 times. If the above-mentioned alcohol solution amount used is out of the above-mentioned range, the crystallization efficiency decreases, which results in reduction in the yield and purity.

In addition, if the cooling temperature of the above-mentioned alcohol solution is below 5° C., the size of crystal grain does not grow enough due to a very fast crystal formation. Conversely, if it is above 20° C., GPC remains in the residual water and alcohol after concentration, which causes the crystallization yield to decrease.

C) Crystallization Step

Type I and Type II crystals are separated by the final crystallization step. First, if 0.1-0.5 mol % of the Type I crystal of L-alpha-glyceryl phosphoryl choline is added, as the seed crystal, to the alcohol solution of L-alpha-glyceryl phosphoryl choline obtained from the above-mentioned B) step, the solution is aged while stirred at 30-60 rpm for 2 to 5 hours, and then the extracted crystal is filtered, Type I crystal of anhydrous form is obtained.

According to the results of the present inventors, it may be possible to obtain Type I crystal without feeding the above-mentioned seed crystal. In this case, however, the above-mentioned alcohol solution should be cooled below −5° C. and the size of crystal grain does not grow enough. In addition, care should be taken since Type II crystal is also formed together if agitation is not provided during the above-mentioned aging process. The first Type I crystal acquired by the present inventors was prepared without using the seed crystal.

Meanwhile, if 0.1-0.5 mol % of the Type II crystal of L-alpha-glyceryl phosphoryl choline is added, as the seed crystal, to the alcohol solution of L-alpha-glyceryl phosphoryl choline obtained from the above-mentioned B) step, the solution is aged without agitation for 2 to 5 hours, and then the extracted crystal is filtered, Type II crystal of monohydrate form is obtained.

According to the results of the present inventors, it may be possible to obtain Type II crystal without feeding the above-mentioned seed crystal. In this case, however, the aging time takes more than 24 hours and the size of crystal grain does not grow enough. In addition, care should be taken since Type I crystal is also extracted together if agitation is provided during the above-mentioned aging process. The first Type II crystal acquired by the present inventors was prepared without using the seed crystal.

Like this, in the present invention, around the seed crystal during the aging process, the size of crystal grain grows to 95-115 μm in case of Type I crystal and to 200-300 μm in case of Type II crystal. If the size of crystal grain grows like this, the hygroscopic property relatively decreases due to reduction in the total surface area of powder.

Hereunder, desirable examples are described in order to assist in understanding of the present invention. However, the right extent of the present invention is not limited due to the examples mentioned below.

Example 1

The liquid L-alpha-glyceryl phosphoryl choline with a water content of 18% (1.5 kg) was concentrated in vacuum at 50° C. for 9 hours to decrease the water content to about 7%. Here, 3 liter of ethanol was fed and agitation was provided, while the temperature was maintained at 50° C., for complete dissolution. And then impurities were removed by using 1.0 μm membrane filter.

Next, after the above-mentioned L-alpha-glyceryl phosphoryl choline solution was cooled to 9° C. and 2 g of Type I crystal of L-alpha-glyceryl phosphoryl choline was fed as the seed crystal, the solution was aged for 2 hours with an agitation of 50 rpm. The crystal extracted this way was filtered and vacuum-dried to obtain 1.04 kg (yield: 85%) of Type I crystal of L-alpha-glyceryl phosphoryl choline with a water content of 0.1%.

Example 2

The liquid L-alpha-glyceryl phosphoryl choline with a water content of 18% (1.5 kg) was concentrated in vacuum at 50° C. to decrease the water content to about 9%. Here, 3 liter of ethanol was fed and agitation was provided, while the temperature was maintained at 50° C., for complete dissolution. And then impurities were removed by using 1.0 μm membrane filter Next, after the L-alpha-glyceryl phosphoryl choline solution was cooled to 10° C. and 2 g of Type II crystal of L-alpha-glyceryl phosphoryl choline was fed as the seed crystal, the solution was aged for 4 hours without agitation. The crystal extracted this way was filtered and vacuum-dried to obtain 1.02 kg (yield: 83%) of Type II crystal of L-alpha-glyceryl phosphoryl choline with a water content of 6.5%.

Comparative Example

The liquid L-alpha-glyceryl phosphoryl choline (30 g) with a water content of 18% was concentrated in vacuum at 50° C. and 60 g of ethanol was added for azeotropic distillation to reduce the water content to 4%, which was confirmed. The solution was then cooled to 5° C. and the formed crystal was aged for 1 hour. Then, the extracted crystal was filtered and dried in vacuum to obtain 17 g (yield: 69%) of the polymorphic crystal of L-alpha-glyceryl phosphoryl choline with a water content of 2.9%.

For reference, in this comparison Example, the crystallization method in J. Am. Chem. Soc. 70, 1394-1399 (1948) and Korean Patent No. 262,281 was implemented.

[Crystal Analysis and Property Test]

A. Powder X-Ray Diffraction (XRD) Analysis

Figure 1:
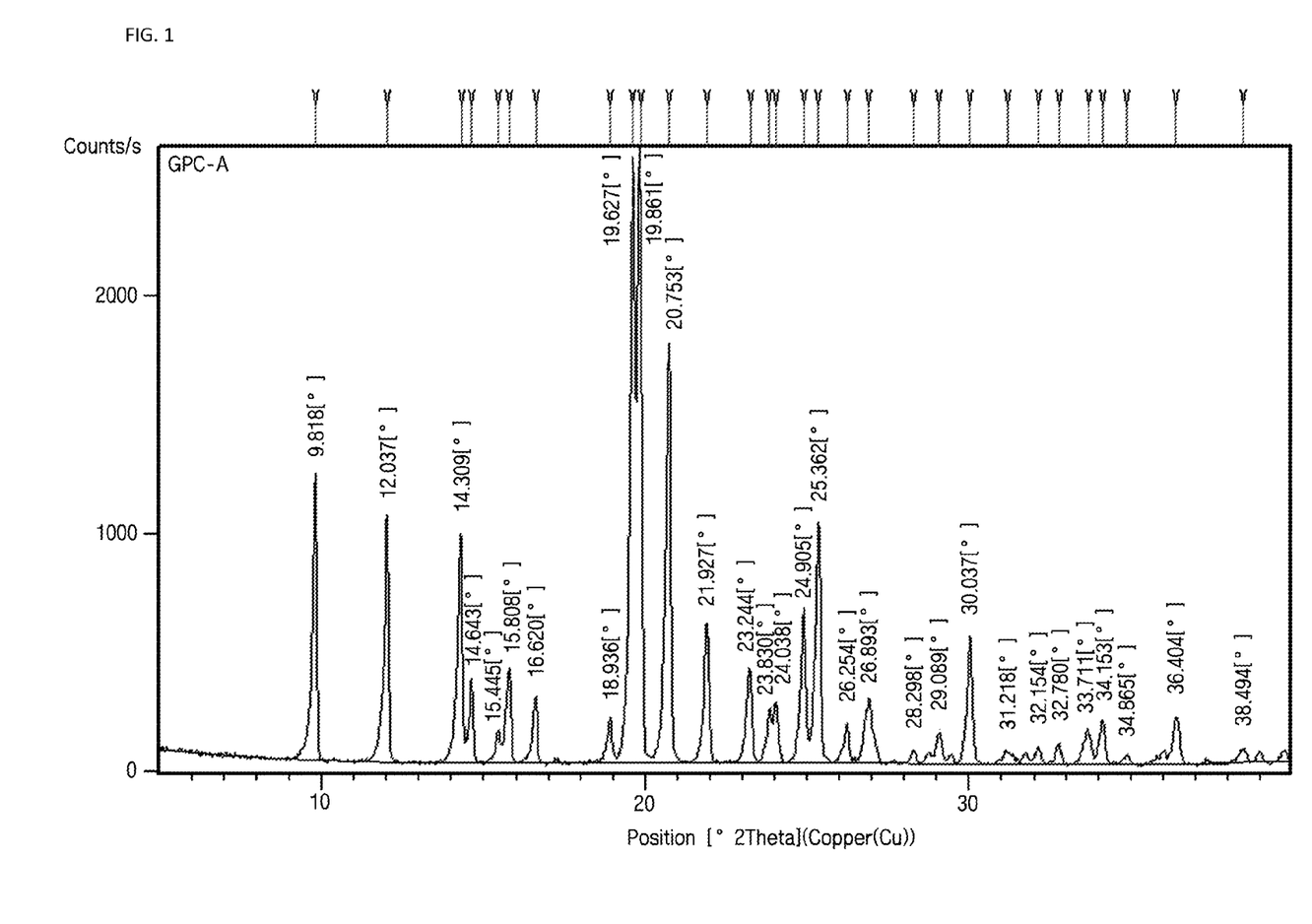
FIG. 1 X-ray diffraction spectrum of GPC Type I crystal in the present invention
FIG. 2 X-ray diffraction spectrum of GPC Type II crystal in the present invention
FIG. 3 X-ray diffraction spectrum of conventional GPC polymorphic crystal
FIG. 4 Differential scanning calorimetric spectrum of GPC Type I in the present invention
FIG. 5 Differential scanning calorimetric spectrum of GPC Type II in the present invention
FIG. 6 Differential scanning calorimetric spectrum of conventional GPC polymorphic crystal
FIG. 7 Graphs for comparison in hygroscopic property between GPC Type I, GPC Type II and polymorphic crystal
FIG. 8 IR spectrum of GPC Type I, GPC Type II and polymorphic crystal
Figure 2:
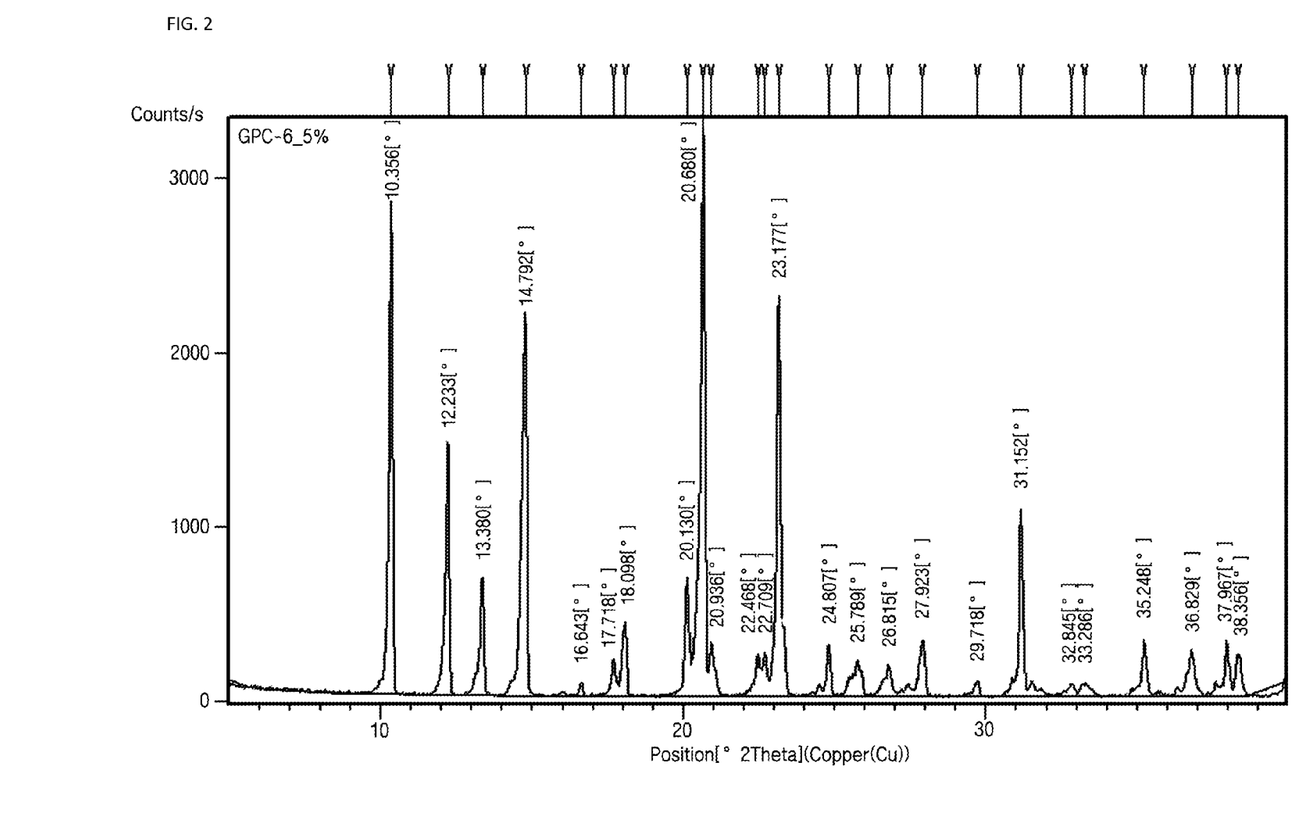

According to the results for the powder X-ray diffraction (XRD) analysis on the GPC crystal obtained in the above-mentioned examples, the 2Θ-diffraction angle of Type I crystal showed peaks at 9/8±0.2°, 12.0±0.2°, 14.3±0.2°, 15.8±0.2°, and 19.6±0.2° as shown in FIG. 1 and that of Type II crystal at 10.3±0.2°, 12.2±0.2°, 13.4±0.2°, 14.8±0.2°, and 20.6±0.2° as shown in FIG. 2.

In addition, according to the results for the powder X-ray diffraction (XRD) analysis on the GPC polymorphic crystal obtained in the above-mentioned comparison Example, the 2Θ-diffraction angle showed peaks at 9.8±0.2°, 12.0±0.2°, 13.4±0.2°, 14.3±0.2°, 14.8±0.2°, 15.8±0.2°, and 19.9±0.2°.

Figure 3:
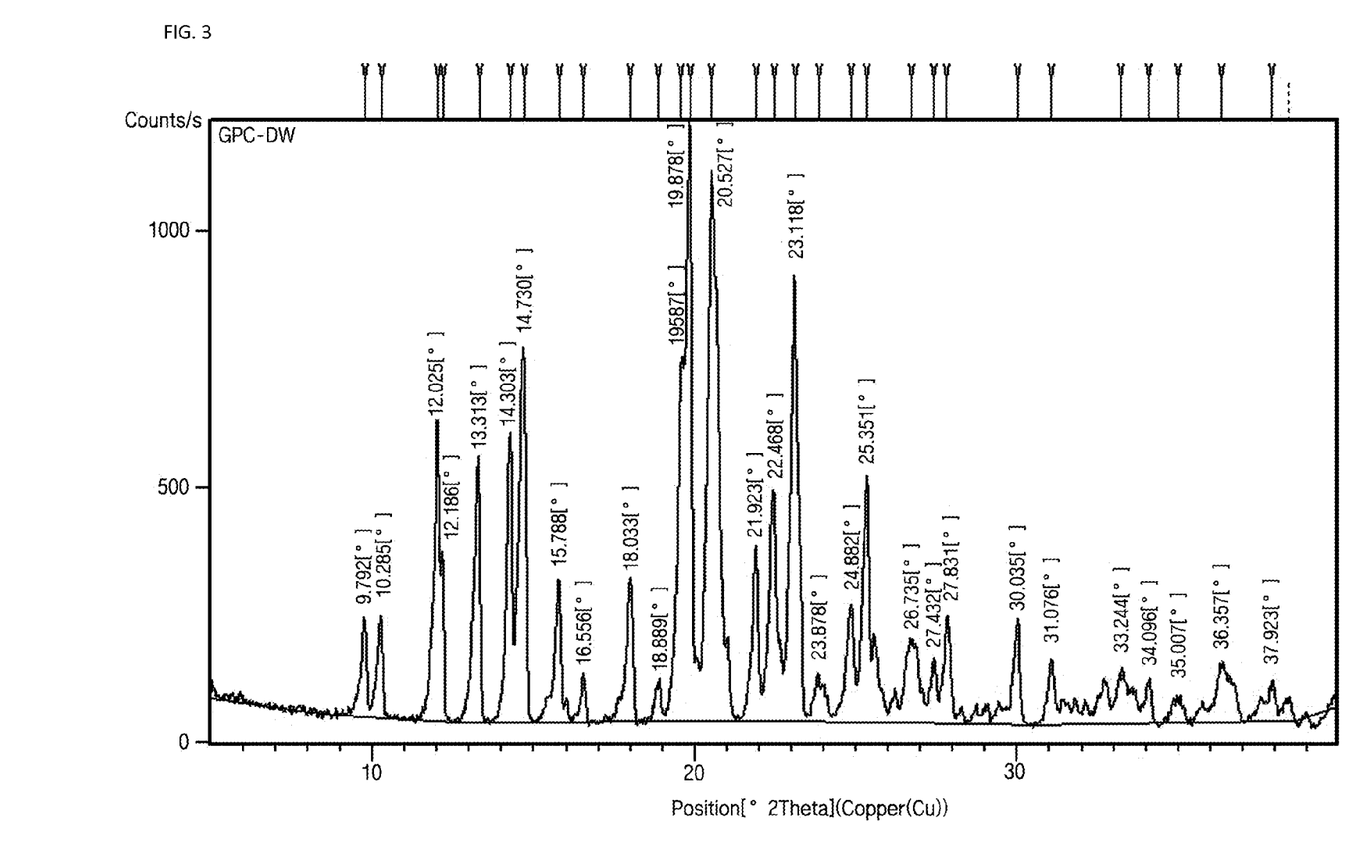
Figure 4:
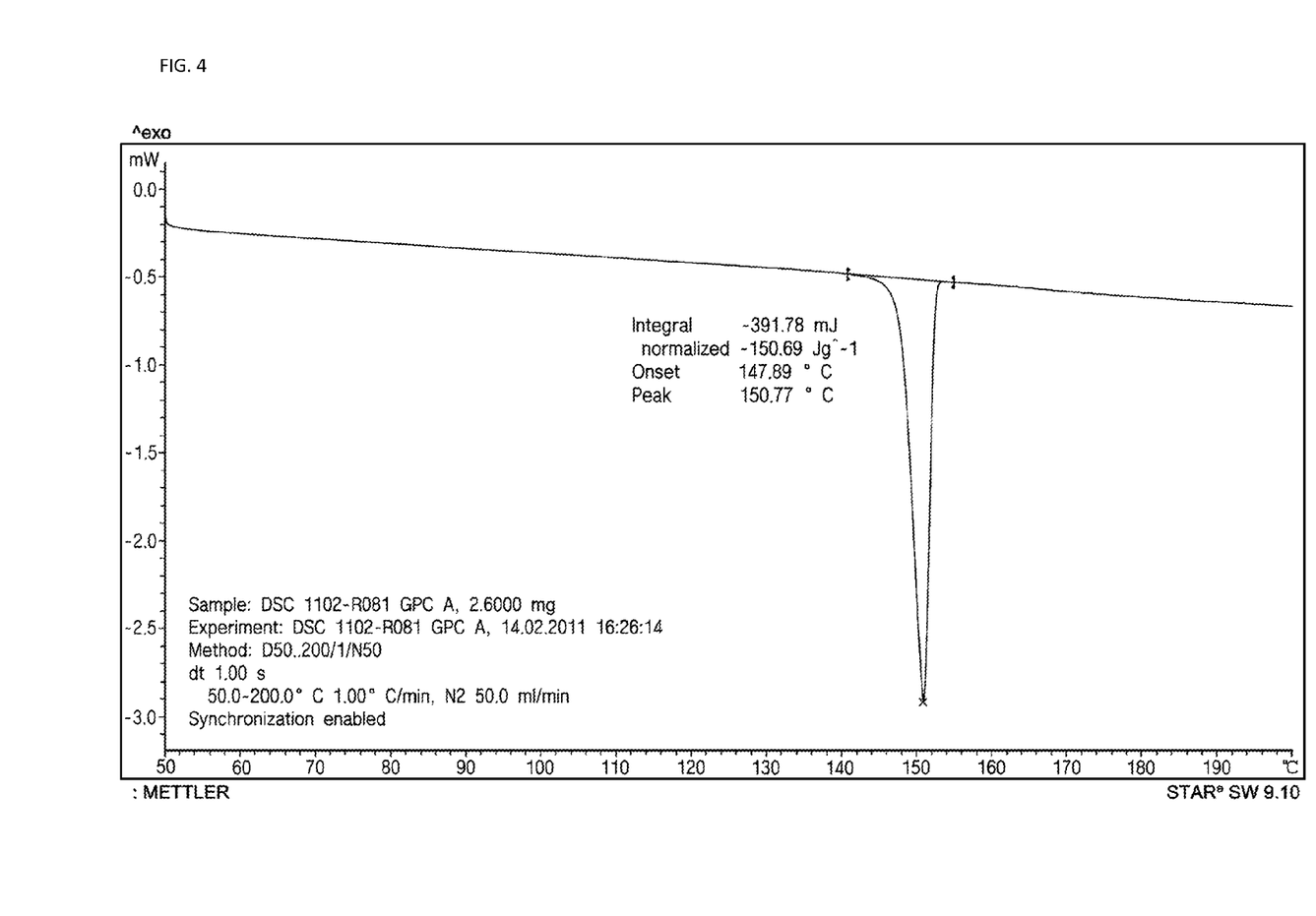
Figure 5:
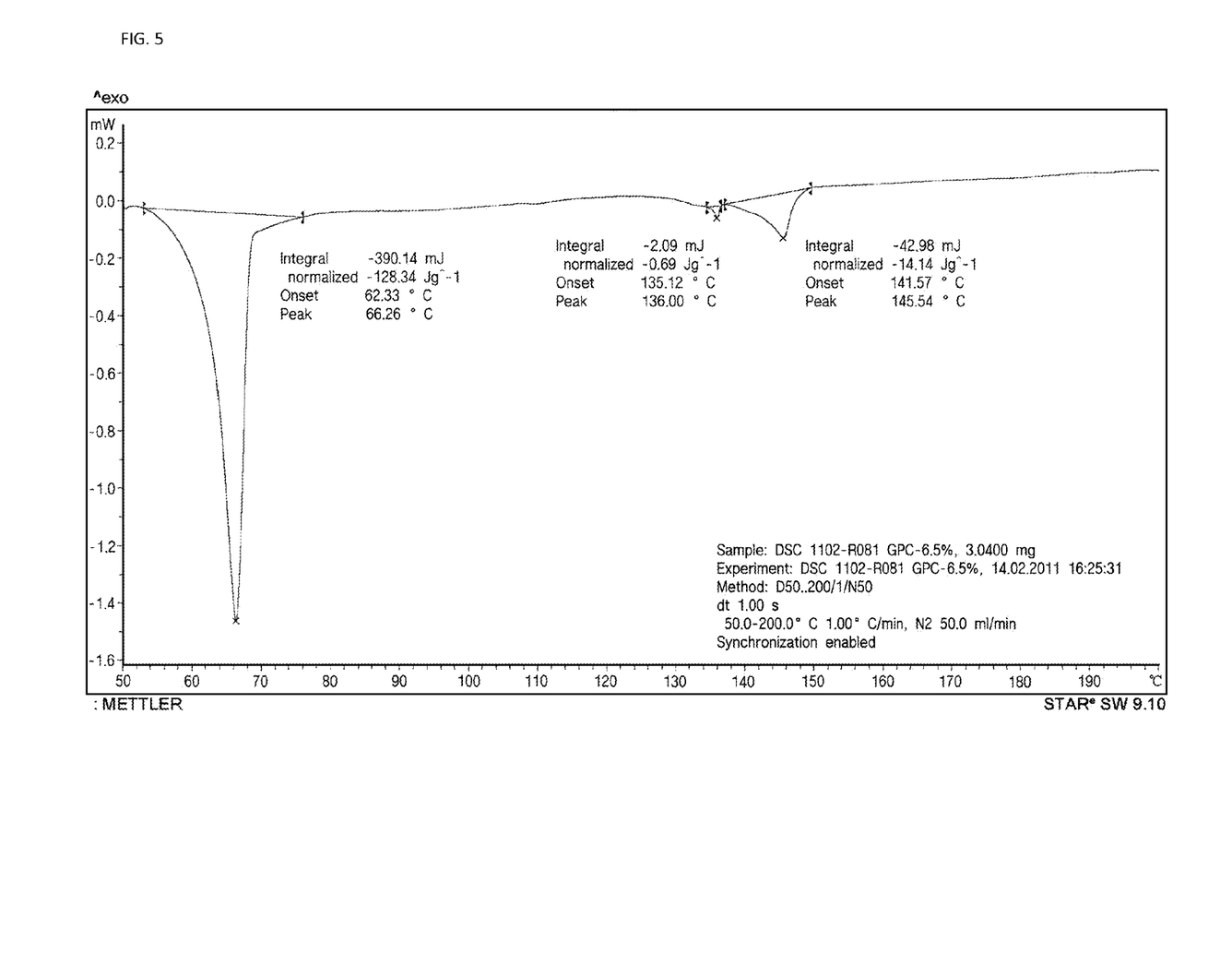

The measurement conditions for the above-mentioned powder X-ray diffraction (XRD) spectrum are as follows:
1) Equipment: PANalytical, X'Pert-Pro/X-Ray Source: Cu
2) Tube Voltage: 40 kV/Tube Current: 30 mA
3) Emission Slot: ½°/Scattering Slot: ½°/Light Receiving Slot: 0.15 mm
4) Scanning Zone: 5 to 40° 2Θ/Sampling Interval: 0.02°
5) Scanning Speed: 0.02°/second B. Differential Scanning Calorimetry (DSC) Analysis According to the results for the differential scanning calorimetry (DSC) analysis on the GPC crystal obtained in the above-mentioned examples, Type I crystal showed an onset temperature of 147° C. and an absorption peak of 150° C. as shown in FIG. 3, and Type II crystal showed an onset temperature of 62° C./an absorption peak of 66° C. and an onset temperature of 141° C./an absorption peak of 145° C. as shown in FIG. 5.

Figure 6:
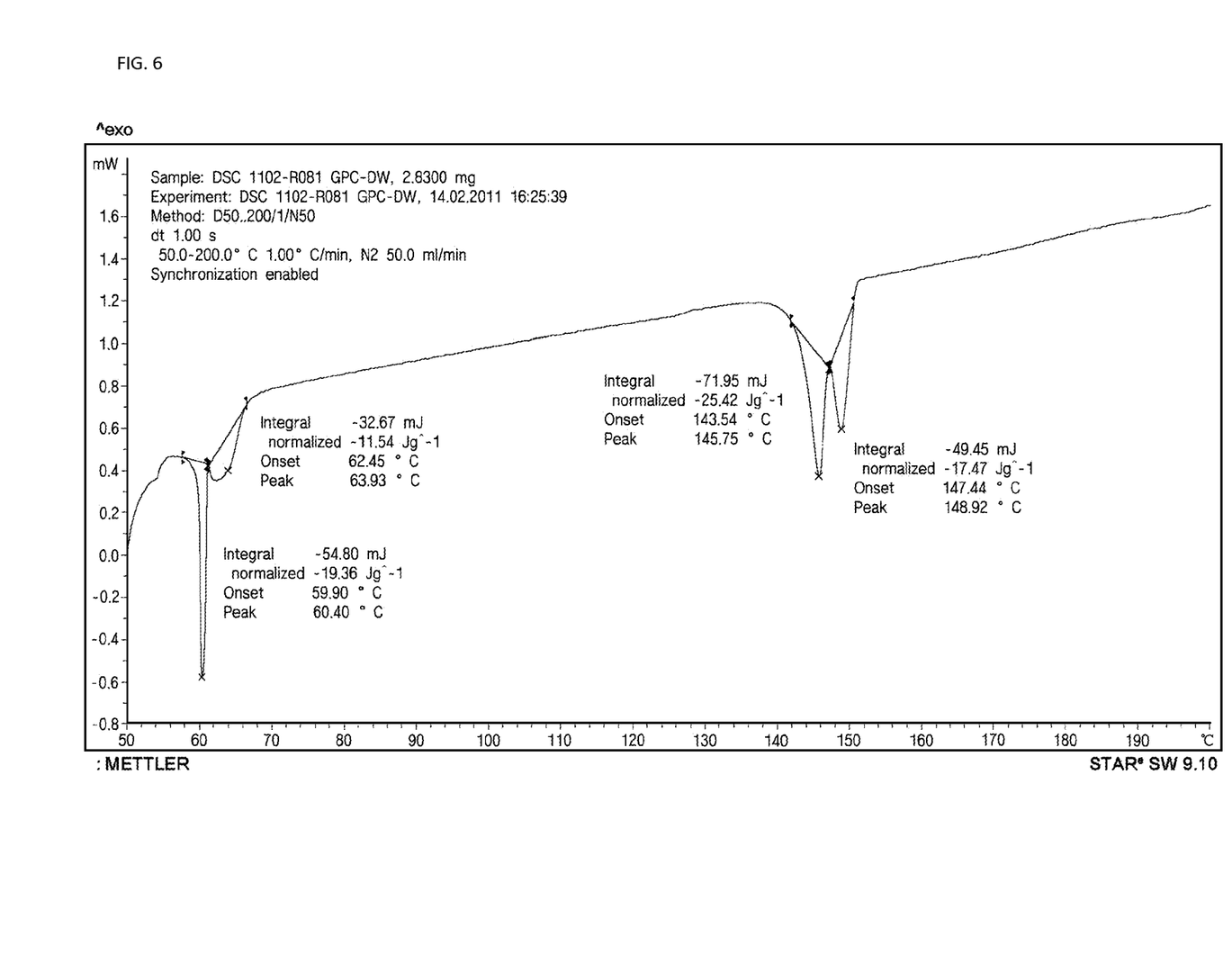

According to the results for the differential scanning calorimetry (DSC) analysis on the GPC polymorphic crystal obtained in the above-mentioned comparison, the polymorphic crystal showed an onset temperature of 60° C./an absorption peak of 60.4° C., an onset temperature of 62° C./an absorption peak of 64° C., an onset temperature of 143° C./an absorption peak of 146° C., and an onset temperature of 147° C./an absorption peak of 149° C. as shown in FIG. 6.

The measurement conditions for the above-mentioned differential scanning calorimetry (DSC) spectrum are as follows:
1) Equipment: Mettler DSC 1102-R081,X
2) Measurement Range: 50 to 200° C./Temperature Rising Interval: 1° C./min
3) N2 Speed: 50 ml/min C. Microphotography The results for the microphotography (magnification: ×100) of the above-mentioned GPC crystals confirmed that Type I crystal has the tetrahedral form of the tetragonal system in which each crystal grain grows uniformly in a size of 95 to 115 μm, forming a smooth grain surface, and Type II crystal has the polyhedral form of the hexagonal system in which each crystal grain grows uniformly in a size of 200 to 300 μm, also forming a smooth gain surface.

However, it was confirmed that, in the polymorphic crystal obtained in the above-mentioned comparison, the crystal grain with a size of 20 to 25 μm agglomerates to make a lump with a size of 150 to 160 μm, forming rough bumps on the surface.

D. Hygroscopicity Test

Figure 7:
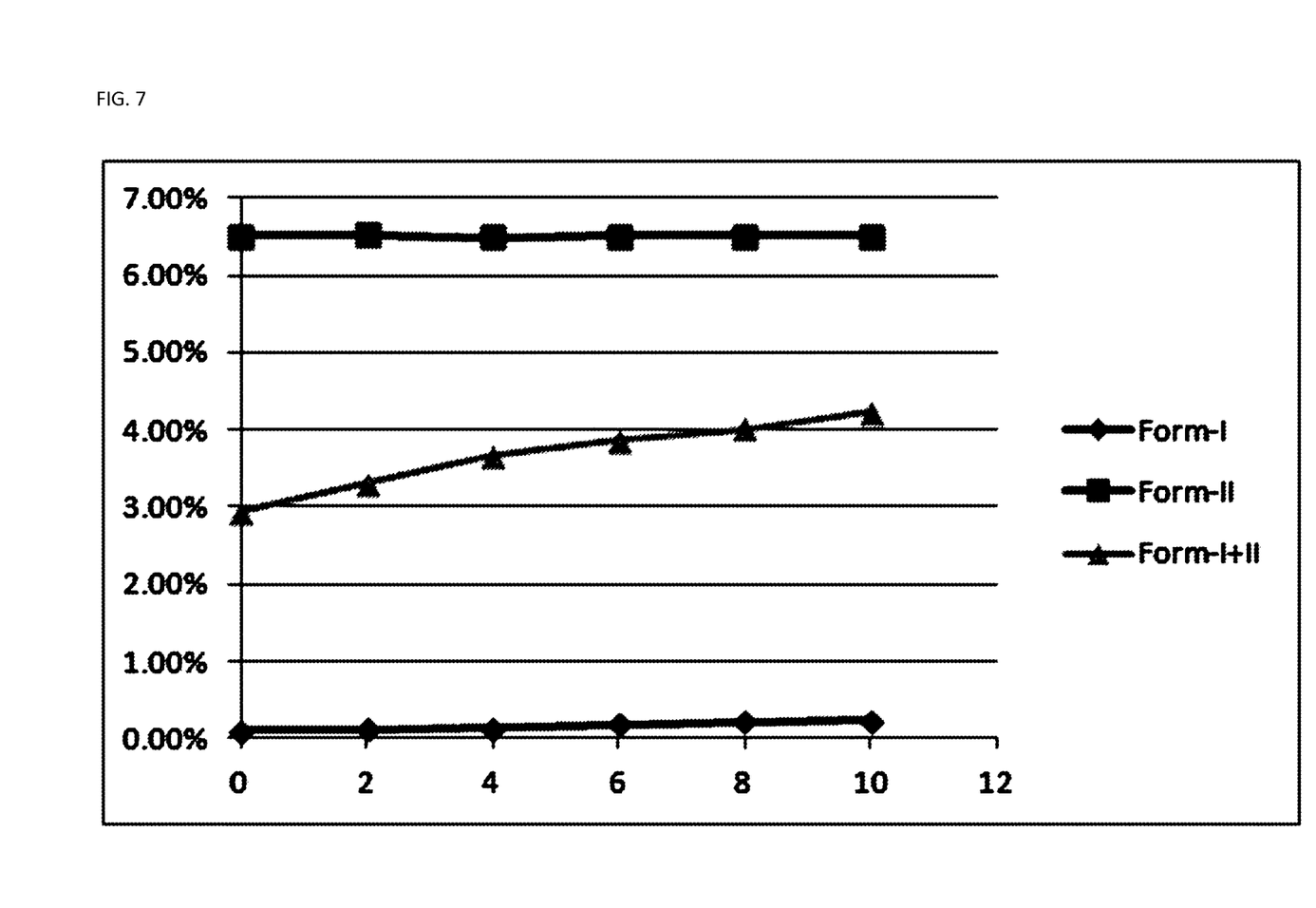

FIG. 7 shows the graphs for the water content change with the passage of time for GPC Type I crystal, GPC Type II crystal, and polymorphic crystal which are left under a humidity condition of 30% for 10 hours. In the figure, X axis indicates the elapse time and Y axis the water content. The above-mentioned Type I crystal and Type II crystal maintained the initial water contents as they are even after passage of 10 hours, indicating a very low hygroscopicity.

In case of the polymorphic crystal, however, the initial water content was 2.9% but increased to 4.2% after 10 hours due to absorption moisture from air. In comparison with Type I and Type II crystals, the high hygroscopicity of the polymorphic crystal is considered to result from rough bumps on the crystal surface.

E. Infrared (IR) Absorption Spectrum

Figure 8:
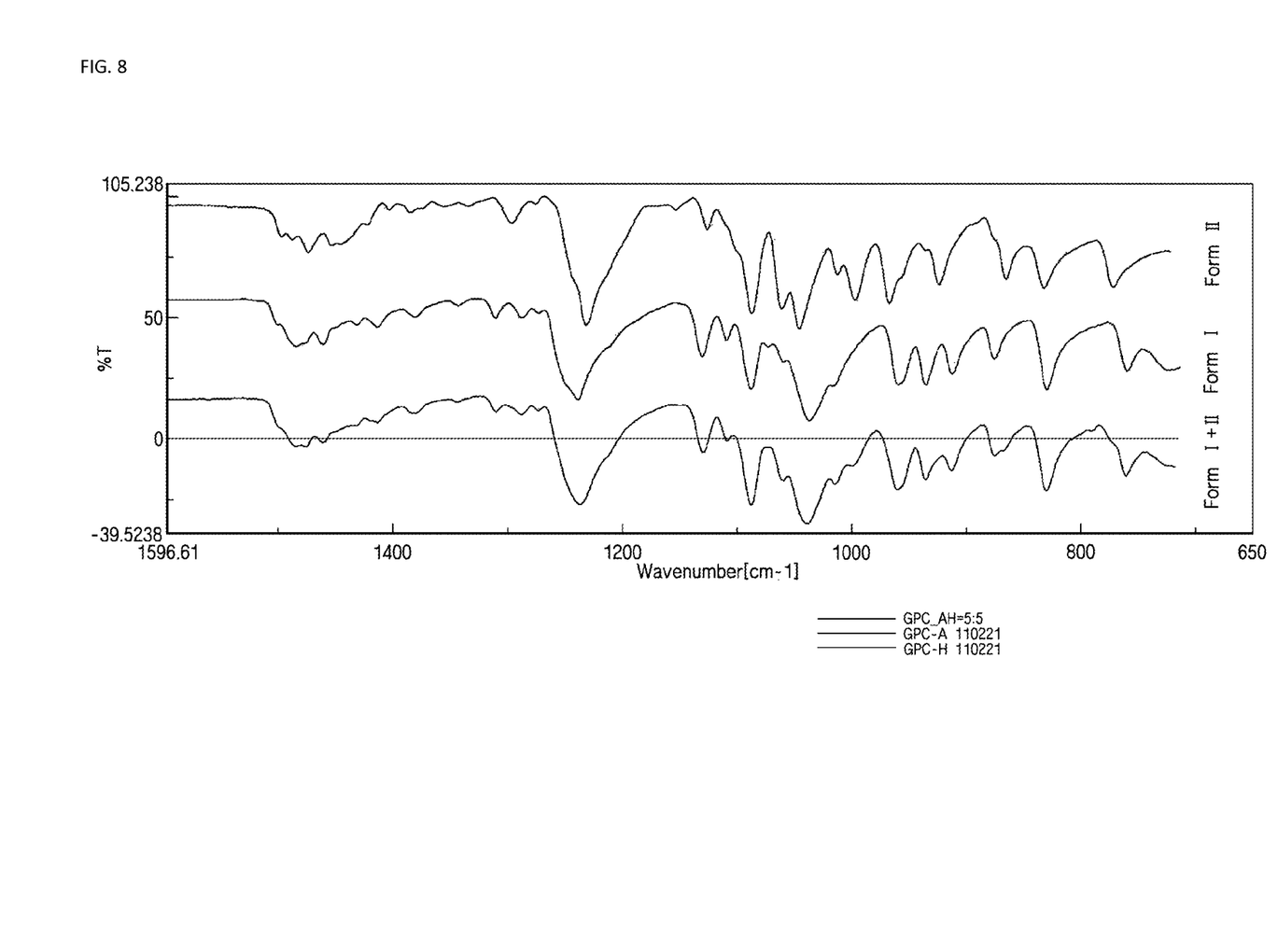

Finally, FIG. 8 shows the measurement for each infrared (IR) spectrum of GPC Type I crystal, GPC Type II crystal and the polymorphic crystal. While Type I and Type II crystals have their unique absorption spectra, the polymorphic crystal is found to possess all the characteristics of Type I and II crystals.

The measurement conditions for the above-mentioned infrared (IR) absorption spectrum are as follows:
1) Equipment: FT/IR-4100 (Jasco)
2) Measurement Range: 4000 to 650 cm-1
3) Resolution: 4.00 cm-1
4) Number of Scans: 36

The invention claimed is:

1. Type I crystal of L-alpha-glyceryl phosphoryl choline, wherein an onset temperature is 147° C. and an absorption peak is 150° C. in a differential scanning calorimetry (DSC) analysis,
wherein 2Θ-diffraction angles of a diffraction pattern are 9/8±0.2°, 12.0±0.2°, 14.3±0.2°, 15.8±0.2°, and 19.6±0.2° in an X-ray diffraction (XRD) analysis, and
wherein the Type I crystal of L-alpha-glyceryl phosphoryl choline, as an anhydride, has a tetrahedral structure of a tetragonal system.

2. A method of manufacturing the Type I crystal of L-alpha-glyceryl phosphoryl choline of claim 1, the method comprising;
A) decreasing water content of ordinary L-alpha-glyceryl phosphoryl choline to 6-12% by concentrating the ordinary L-alpha-glyceryl phosphoryl choline at 45-65° C.;
B) dissolving the concentrated L-alpha-glyceryl phosphoryl choline obtained in step A) in an alcohol solution, an amount of the alcohol solution being 1 to 5 times an amount of the concentrated choline and then cooling the entire solution to 5-20° C.; and
C) feeding, as a seed crystal, 0.1 to 0.5 mol % of the Type I of L-alpha-glyceryl phosphoryl choline into the alcohol solution of L-alpha-glyceryl phosphoryl choline obtained in step B), aging the entire solution for 2-5 hours while stirring at 30-60 rpm, and then filtering the extracted crystal.

3. The method according to claim 2,
wherein the concentrated L-alpha-glyceryl phosphoryl choline of step A) has the water content of 15 to 18% originally and concentrated for 8 to 10 hours.

4. The method according to claim 2,
wherein the concentrated L-alpha-glyceryl phosphoryl choline of step B) is dissolved in ethanol or isopropanol, an amount of the ethanol or isopropanol being 2 to 5 times the amount of the concentrated choline.

* * * * *